United States Patent [19]

Hall

[11] Patent Number: 5,758,662
[45] Date of Patent: Jun. 2, 1998

[54] DEVICE FOR SHIELDING AN INCISION

[76] Inventor: J. Rodney Hall, 290 Blucher Cir., Lake Wylie, S.C. 29710

[21] Appl. No.: 691,323

[22] Filed: Aug. 2, 1996

[51] Int. Cl.$^6$ ............................................. A61F 13/00
[52] U.S. Cl. ................................. 128/888; 128/889
[58] Field of Search .................... 128/846, 869, 128/882, 888, 889; 602/41, 47, 59; 63/4, 21

[56] References Cited

U.S. PATENT DOCUMENTS

| | | |
|---|---|---|
| 695,270 | 3/1902 | Beringer . |
| 2,056,767 | 10/1936 | Blath ................................. 128/889 |
| 2,250,741 | 7/1941 | Baruch ................................. 63/4 |
| 2,520,436 | 8/1950 | Russell . |
| 3,334,626 | 8/1967 | Schimmel . |
| 4,000,737 | 1/1977 | Horn . |
| 4,159,021 | 6/1979 | Casburn ................................. 128/889 |
| 4,905,681 | 3/1990 | Glascock ................................. 128/888 |
| 5,060,662 | 10/1991 | Farnsworth, III . |
| 5,072,738 | 12/1991 | Wonder et al. . |
| 5,101,837 | 4/1992 | Perrin ................................. 128/888 |

*Primary Examiner*—Michael A. Brown
*Attorney, Agent, or Firm*—Kennedy Covington Lobdell & Hickman, LLP

[57] ABSTRACT

A device for shielding a surgical incision or other sensitive area of the body from contact with clothing or other items. The shielding device has a protective member including a substantially rigid frame, a plurality of substantially rigid support legs, each of which extend from the protective frame in an angular relation toward the body of the user and terminate in a contact end and a plurality of contact elements on the contact end of each of said support legs for contacting the body of the user. The device also includes a flexible support loop attached to the protective member and forming a loop for placing around the neck of the user to suspend the protective member from the user's neck and position it over the area to be shielded. The support elements may include a disc-shaped member which has a contact face with a surface having a convex curvature for contacting the body of the user, and the surface of the contact face may have a relatively low coefficient of friction for contacting the body of the user in substantially non-frictional engagement. The frame may be a lightweight rod material which forms the perimeter of a substantially planar geometric shape and the frame may form a quadrilateral having rounded corner portions with each of the support legs fixed to one of the corner portions.

10 Claims, 6 Drawing Sheets

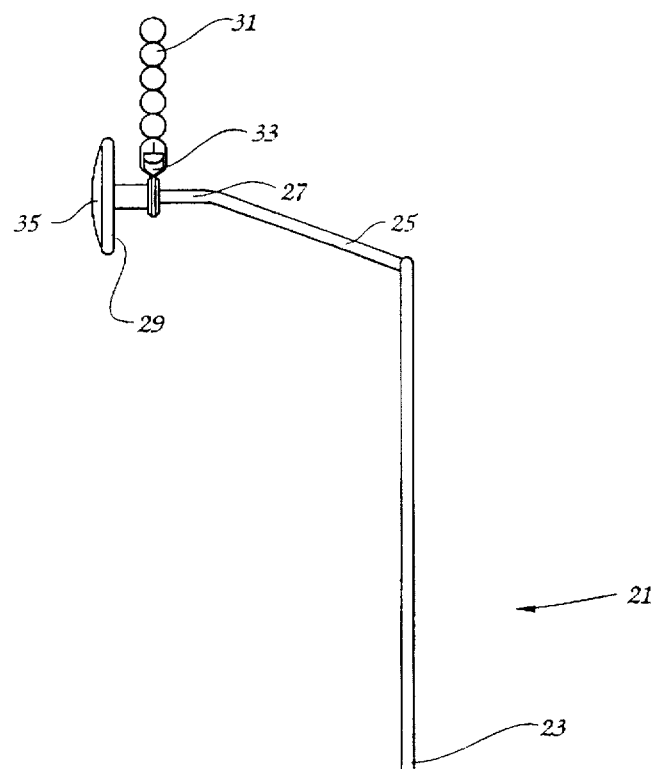
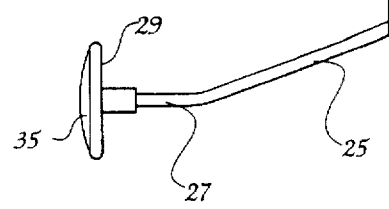

DEVICE FOR SHIELDING AN INCISION

BACKGROUND OF THE INVENTION

The present invention relates generally to devices for protecting a portion of the human body and, more particularly, to a device for shielding a sensitive area of the body, such as the site of a recent incision, from unwanted contact with clothing, bedding, or other material.

Heart surgery and other operations involving the chest cavity or abdomen can leave large incisions which take some time to heal. During the healing process, the area of the incision will be extremely sensitive and contact with the area by clothing or other materials can cause great discomfort. Typically, a larger incision will not be covered with bandages or a dressing which might provide protection but, rather, will be left uncovered to promote air circulation across the area of the incision, which furthers the healing process and reduces the risk of infection.

Previous attempts have been made to provide protective devices or shields which would prevent contact with the sensitive area of the incision, while allowing air circulation with its healing benefits, but all known devices suffer from various drawbacks. Warnecke et al U.S. Pat. No. 4,023,569 discloses a device for protecting wounds which consists of a shallow bowl formed from grid-like material having apertures formed therein. The bowl has a flat rim which is attached to the skin surrounding the sensitive area to be protected either by means of adhesive adhering to the skin or by a dressing fixed to the skin. Either of these methods of holding the Warnecke et al device in place would cause binding and pulling on the user's skin during any appreciable movement of the body as a result of the adhesive gripping the skin, and both would require effort to remove the device. Moreover, removal of the Warnecke et al device would also, in either type of attachment, again result in pulling forces on the skin adjacent the sensitive incision site, causing pain and discomfort to the user. This device is also apparently not reusable.

Horn U.S. Pat. No. 4,000,737 discloses a surgical incision shield consisting of a relatively rigid longitudinal strip held in place by relatively rigid U-shaped elements bridging an incision site. The various shield elements in the Horn device are attached to the skin surface by means of adhesive material. The Horn device thus has many of the same disadvantages as the Warnecke et al device, in that it binds the skin at its point of adhesive attachment, which results in pulling forces being exerted on the incision site when the user undertakes all but the most negligible movements. Moreover, removal of the Horn device involves separating the adhesive material from the skin, which again irritates the highly sensitive area of the incision site. This device also does not appear to be reusable.

An open air bandage is disclosed in Farnswoth III U.S. Pat. No. 5,060,662. This bandage comprises a ring of pliable material which is adhered to the skin surrounding the wound to be bandaged, and an arrangement of air-permeable members affixed to the upper side of the ring of pliant material. The adhesive attachment of the Farnswoth III device to the skin creates the same difficulties as seen in Warnecke et al and Horn and is also apparently not reusable.

The incision and wound protective devices previously disclosed therefore have significant disadvantages which create pain and discomfort for users. Moreover, such devices may not be economical in that they are apparently not reusable and must be discarded once removed. While secure positioning of such a protective device is necessary, the use of adhesive as disclosed in the references discussed above creates additional discomfort for the user.

The present invention provides a device for shielding an incision which avoids or alleviates the aforesaid drawbacks of conventional approaches.

SUMMARY OF THE INVENTION

In accordance with the present invention, a device is provided for shielding a sensitive area of a user's body, such as the location of a surgical incision. The device of the present invention comprises a protective member which has a substantially rigid frame, a plurality of substantially rigid support legs extending from the frame in an angular relation toward the body of the user and terminating in a contact end, and a plurality of contact elements disposed on the contact ends of the support legs for contacting the body of the user. A flexible support loop element is attached to the protective member and forms a loop for placing around the neck of the user to suspend the protective member from the user's neck and to position it over the area to be shielded.

It is advantageous if the support elements include a disc-shaped member which has a contact face comprising a surface with a convex curvature and a relatively low coefficient of friction for contacting the body of the user in substantially non-frictional engagement. The frame may comprise lightweight rod material and may also advantageously form the outer perimeter of a substantially planar quadrilateral which has rounded corner portions, with each of the support legs being fixed to one of the corner portions.

The device of the present invention may further include a substantially rigid lightweight panel attached to the frame, and the panel may be perforated to reduce its weight.

The support loop element preferably has two ends, each of the ends being attached to a separate one of the support legs substantially adjacent the contact element on the leg so that the point of connection forms a fulcrum point when the protective member is suspended from the user's neck, with the fulcrum point assisting in holding the protective member against the user's body by gravity.

It is advantageous if the device includes a pair of crosspiece members attached to the frame at the rounded corner portions and generally bisecting the perimeter of the frame, with the support legs formed integrally with the cross-piece members.

Accordingly, the present invention provides a device for shielding a sensitive area of a user's body which can easily be put in place merely by suspending it from the user's neck. The shielding device of the present invention may likewise be readily and easily removed merely by lifting the loop from around the user's neck. Moreover, while in place, the device of the present invention neither binds nor pulls on the skin of the user but, rather, can move in a limited range across the skin of the user, while being restrained from excessive movement through its attachment around the neck of the user.

BRIEF DESCRIPTION OF THE DRAWINGS

FIG. 2 is an side elevational view of the shielding device of FIG. 1;

DESCRIPTION OF THE PREFERRED EMBODIMENT

Figure 1:
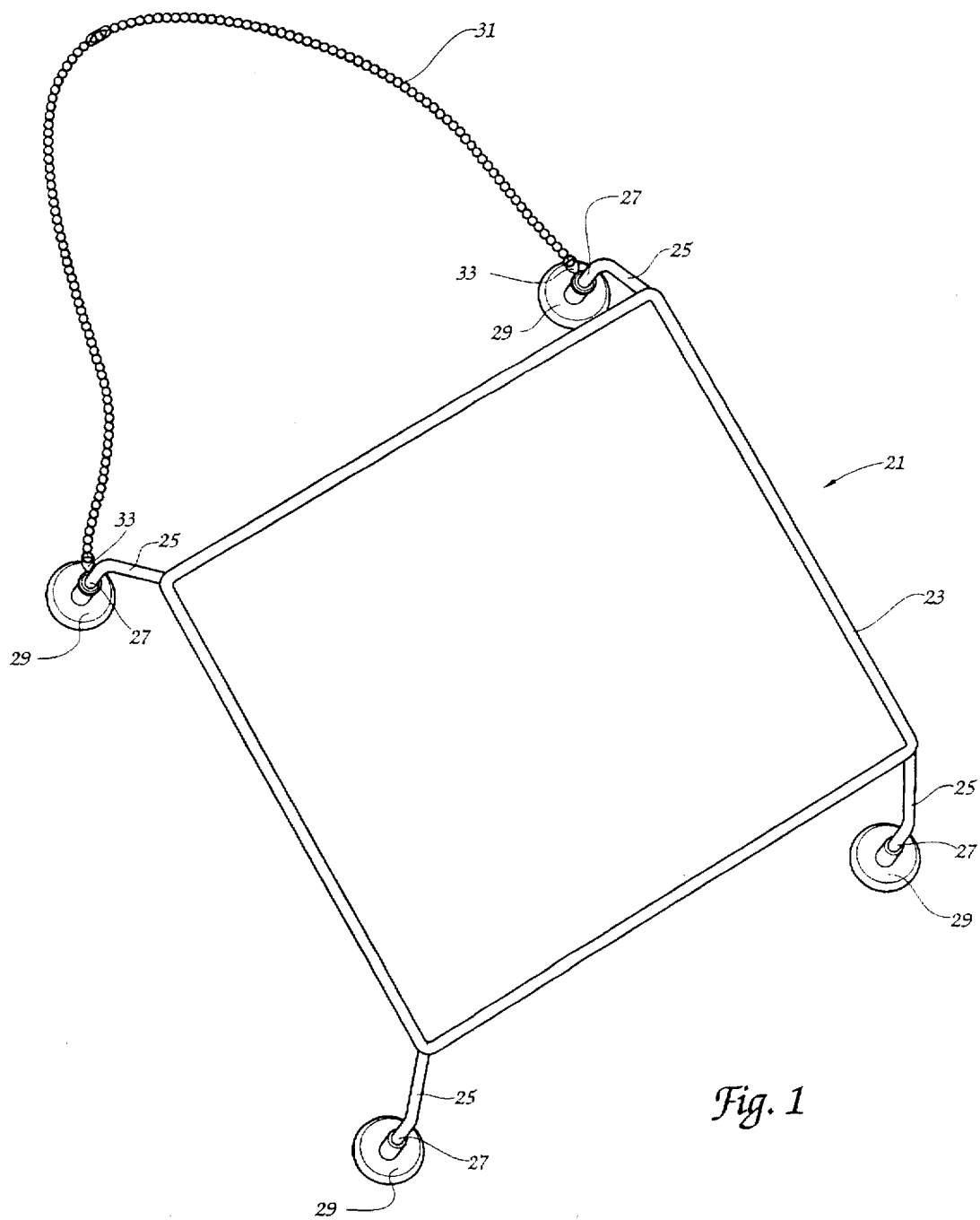
FIG. 1 is a perspective view of the shielding device embodying the present invention.

Looking now in greater detail at the accompanying drawings, FIG. 1 illustrates in perspective view the shielding device 21 of the present invention. The shielding device 21 consists of a protective member including a substantially rigid protective frame 23, four substantially rigid support legs 25, each of which is attached to the frame 23 and terminates in a contact end, and four contact elements 29, each of which is disposed on the contact end 27 of one of the support legs 25. The device of the present invention also includes a loop element in the form of a conventional flexible ball chain 31 which is attached at its two ends to support legs 25 by means of ball chain couplings 33, which are also conventional.

Protective frame 23 and support legs 25 may be formed from stainless steel rod, such as is commonly available from steel supply sources. Stainless steel rod provides sufficient rigidity for protective member 21, but may be bent somewhat to adjust the device to fit different individuals, may be sterilized, does not generally cause allergic reactions, and resists corrosion and other deterioration. The stainless steel rod material forming protective frame 23 and support legs 25 would be joined through conventional means such as welding.

Protective frame 23 and support legs 25 may also be formed from molded plastic or other suitable materials, which may simplify manufacture. In such an embodiment, protective frame 23 and support legs 25 may be molded in one piece to eliminate the necessity of joining such components.

Support elements 29 may be formed as stainless steel or plastic pads for contacting the body of the user. Stainless steel support elements 29 would be joined to support legs 25 by welding or other conventional techniques. Support elements 29 composed of plastic may be molded as an integral part of a plastic protective frame 23 or joined to a stainless steel protective frame 23 through conventional means such as pressure fit or epoxy.

The contact elements 29, as seen in FIG. 2, have a contact surface 35 which has a convex curvature so that it presents little frictional resistance in contacting the body of the user. Contact surface 35 may also be composed of a material which has a relatively low coefficient of friction, such as a polished metal or plastic, to further reduce the frictional resistance of the surface 35.

The construction of shielding device 21 is also arranged so that all four contact elements 29 contact the user's body so as to provide stable support for the shielding device and in turn for clothing or bedding which is held away from the incision 37 by the shielding device 21. As seen in FIG. 2, support legs 25 are connected to ball chain 31 through couplings 33 which, when the shielding device 21 is in place and suspended around the user's neck, are positioned adjacent contact elements 29, as seen in FIG. 2. The coupling 33 may be fixed adjacent contact elements 29 or they may be free to slide on support legs 25 such that they automatically position themselves adjacent contact elements 29 once suspended around the user's neck. Support legs 25 are inclined outwardly from frame 23 to assist the positioning of sliding couplings 33 at the desired location. Placement of the couplings 33 adjacent contact elements 29 causes the couplings 33 to act as fulcrum points when the shielding device 39 is in place around the user's neck, with the result that all of the contact elements 29 are pressed against the body of the user by the force of gravity acting on the shielding device 21 (see FIGS. 2 and 3).

Figure 3:
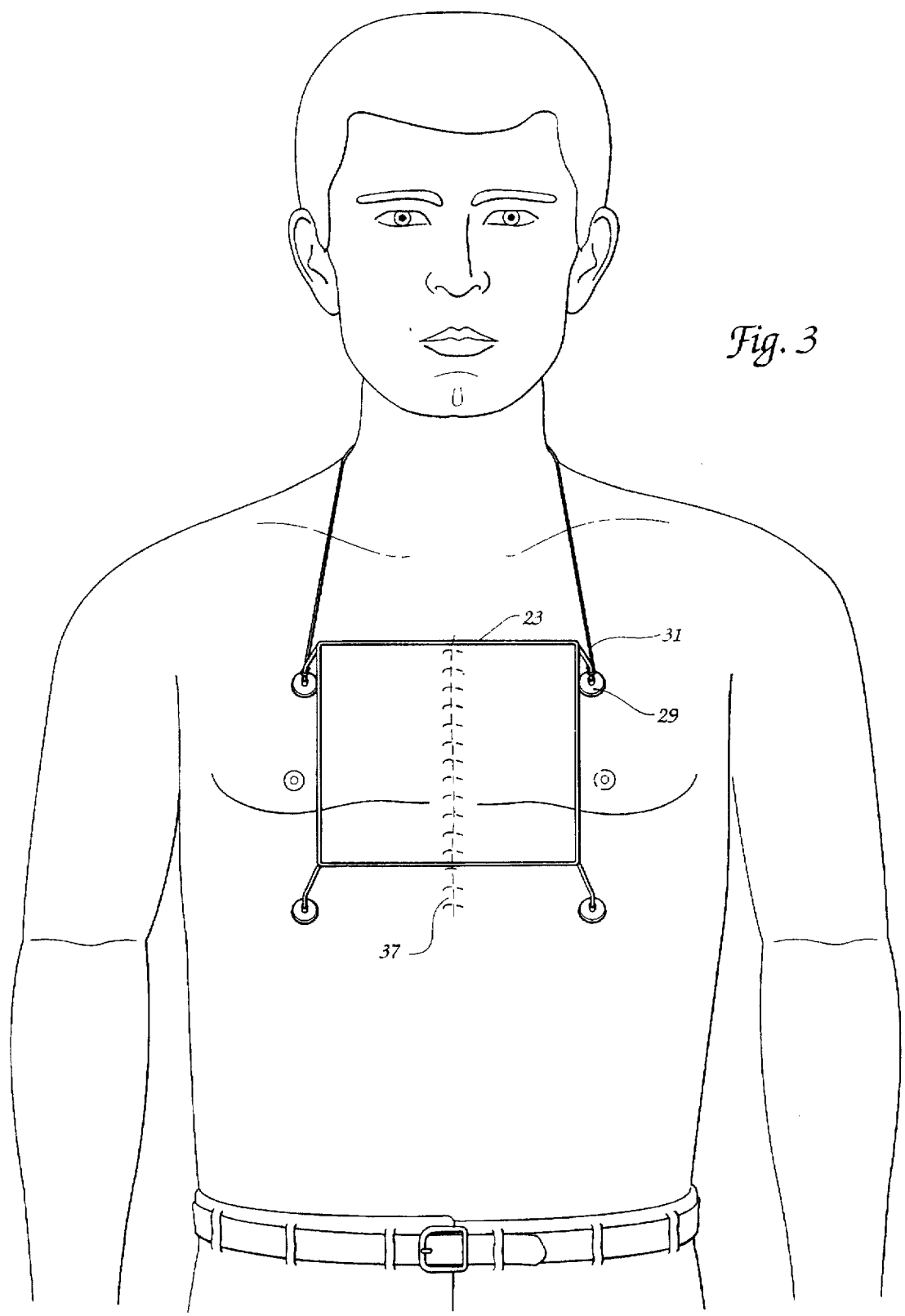
FIG. 3 is a view showing the device of FIG. 1 in place on the body of a user to shield the area of a surgical incision.

In place and positioned around the neck of a user, as seen in FIG. 3, the shielding device of the present invention is supported on the user's chest by contact elements 29 and suspended by ball chain 31 to hold the shielding device 21 in position. The protective frame 23 is located directly over surgical incision site 37 so that clothing worn by the user will be supported above the incision 37 in order to prevent contact with such clothing. Bedding would likewise be supported by the shielding device and held away from incision site 37 to again prevent painful contact with the sensitive area of the incision 37.

Movement by the user would cause some motion of the shielding device 21 as it slides on contact elements 29 across the user's skin. However, such motion of the shielding device 21 is restrained by ball chain 31 placed around the user's neck, and normal movements would not cause the shielding device to move to such an extent that contact elements 29 would touch the sensitive area surrounding the incision 37.

Figure 4:
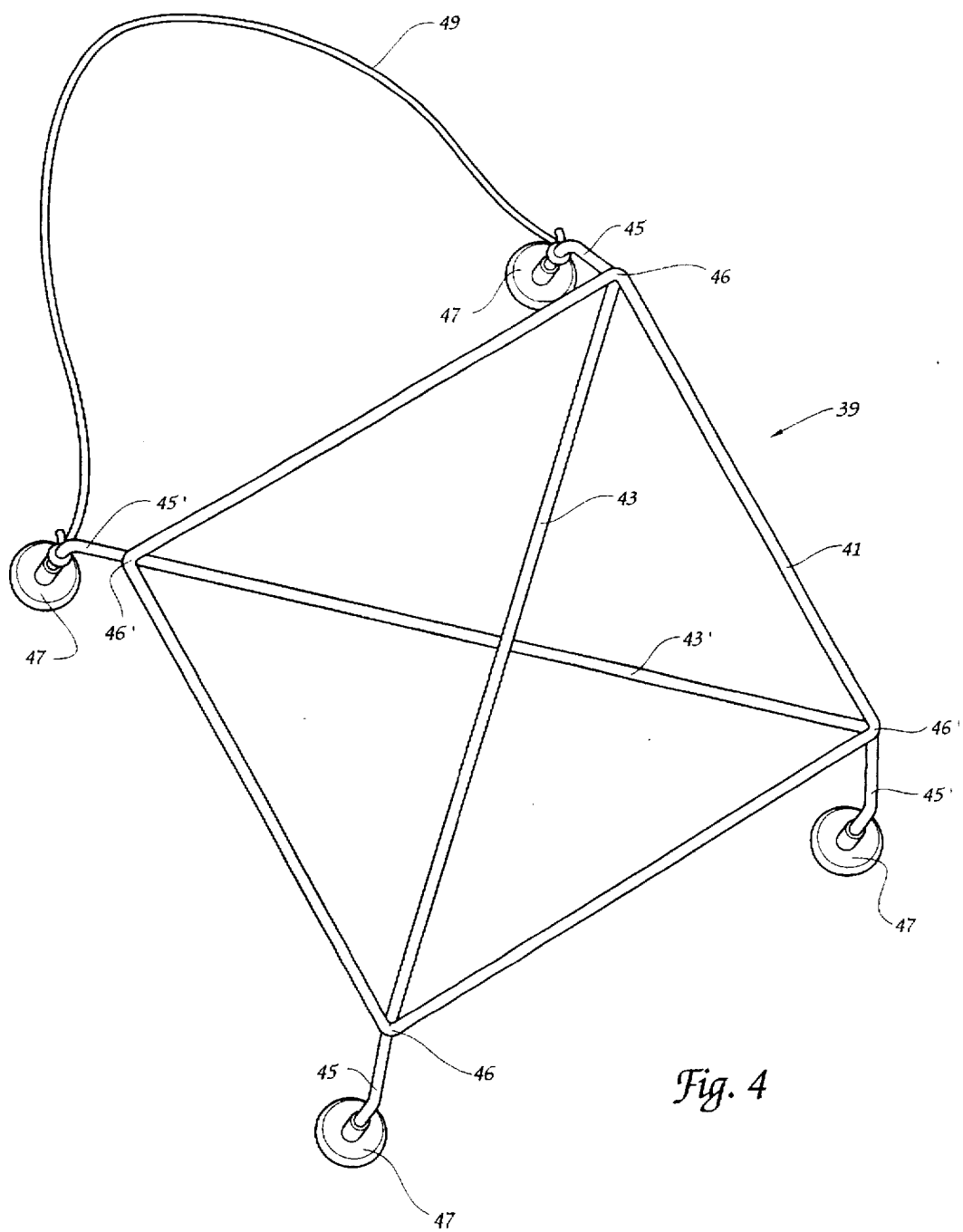
FIG. 4 is a perspective view of a variation of the shielding device of the present invention.

An alternate embodiment of the shielding device of the present invention is shown in FIG. 4, which illustrates a shielding device 39 which consists of a quadrilateral-shaped planar protective frame 41, cross-piece members 43,43', support legs 45 which are formed integrally with cross-piece 43, and support legs 45' which are formed integrally with cross-piece member 43'. Cross-piece members 43,43' are attached to the frame 41 at, respectively, rounded corner portions 46,46'. The shielding device also includes contact elements 47 and support loop 49. In this embodiment, the arrangement by which support legs 45 are formed integrally with cross-piece member 43 and support legs 45' are formed integrally with cross-piece member 43' results in the shielding device 39 having three main substantially rigid structural components consisting of the two cross-piece members 43,43' (along with their associated support legs 45,45') and protective frame 41. These three elements can be joined by conventional means, such as welding of protective frame 41 to cross-pieces 43,43'. Manufacture of shielding device 39 may therefore be simplified, while cross-piece members 43,43' also provide a central shield within the perimeter of protective frame 41 which acts to further prevent contact of clothing or other items with a sensitive incision site.

The embodiment shown in FIG. 4 also includes a loop cord 49 which may be composed of plastic cord or other like flaccid material. Use of such material for loop cord 49 may provide additional comfort and avoid irritation of the user's skin which may be caused by a metal ball chain, and may therefore be preferable for some individuals. Loop cord 49 may be attached to support legs 45,45' through the use of epoxy or other conventional means.

Figure 5:
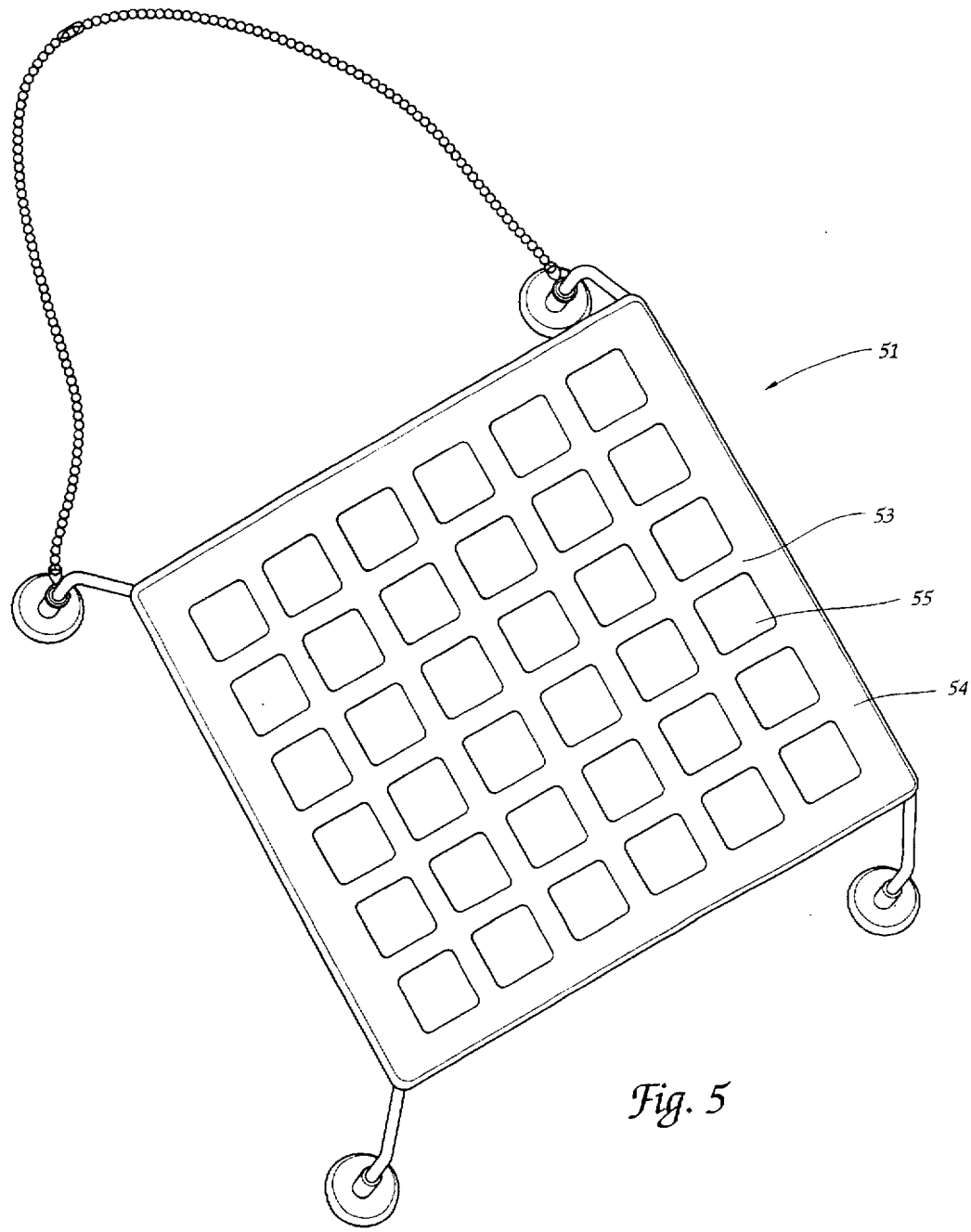
FIG. 5 is a perspective view of another embodiment of the present invention which includes a lightweight perforated panel.

An additional embodiment of the shielding device of the present invention is shown in FIG. 5, which illustrates a shielding device 51 including a substantially rigid perforated panel 53. The panel 53 is composed of a lightweight material such as plastic and further has its weight reduced by means of perforations 55. The panel 53 provides further protection and shielding of the highly sensitive area of a surgical incision from contact by clothing, bedding, and other items.

Figure 6:
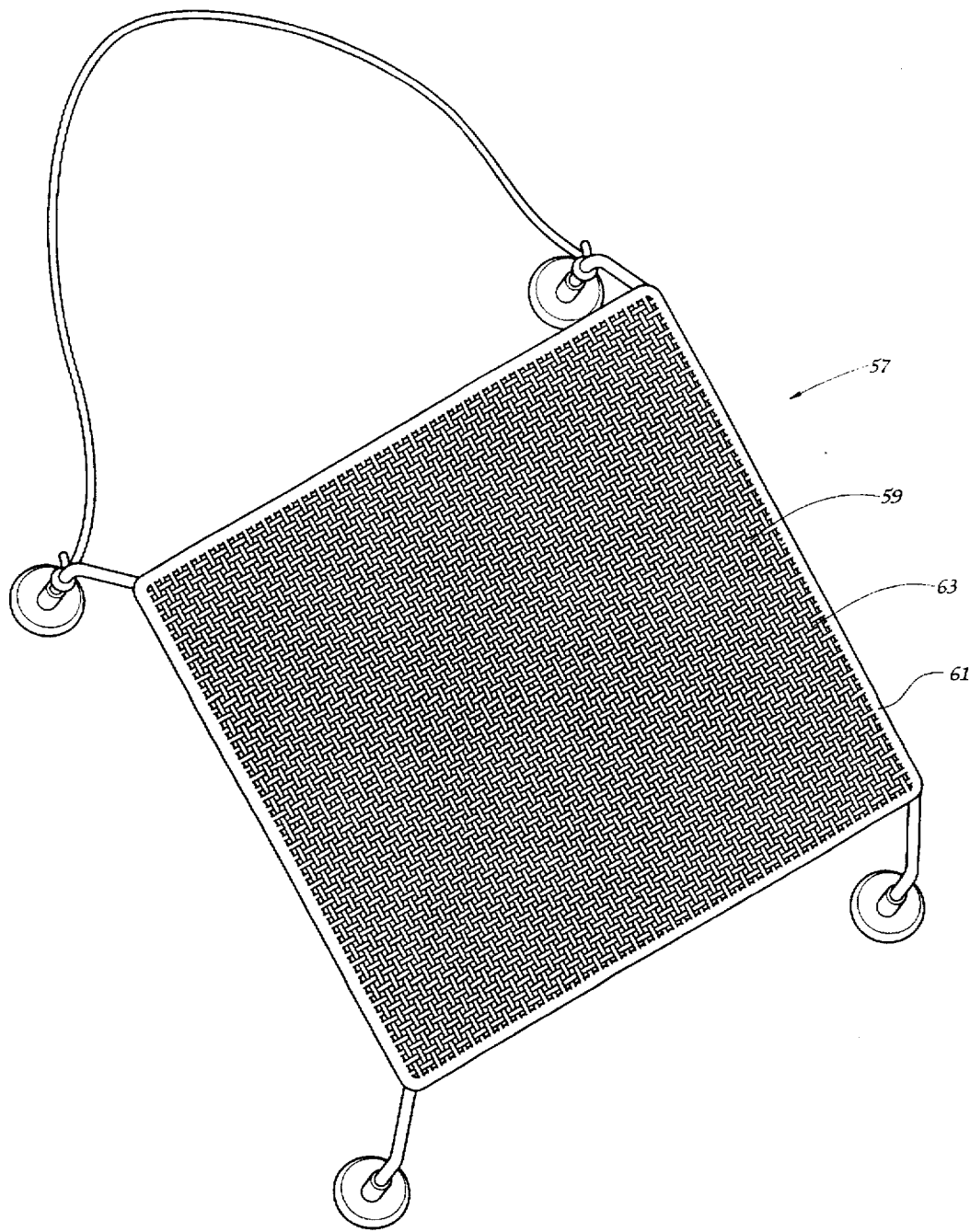
FIG. 6 is a perspective view of another embodiment of the present invention which includes a lightweight fabric panel.

A further embodiment of the present invention is shown in FIG. 6, which depicts a shielding device 57 which includes a fabric panel 59 attached to frame 61. Fabric panel 59, which defines apertures 63, also provides protection for the area of surgical incision without adding significant additional bulk or weight to the shielding device 57. Moreover, apertures 63 permit air circulation over the area of the surgical incision which is known to promote healing of the wound.

The unique advantages of the present invention provide the user with a shielding device that is easily put into position and comfortably worn while allowing the user to move about normally without additional discomfort. Significantly, the shielding device of the present invention requires no adhesive to hold it in place but, rather, maintains its general position by being suspended from a neck loop and supported on the user's body by contact pads which are free to move to a limited extent on the user's body. The shielding device may easily be removed, without requiring detachment of adhesives or other anchoring means. It protects a wide area of skin, such as the incision and surrounding sensitive area resulting from heart surgery or other major operation.

In place, the shielding device is unobtrusive under loose clothing and may also be worn in bed for comfort when sleeping. The shielding device, when constructed from plastic, metal, or other rod material, may be adjusted for comfortable fit on various individuals and may also be constructed in different sizes. The device may be sterilized and reused by different patients if fabricated from stainless steel or other suitable material, increasing the economical benefits gained from use of the device.

It will therefore be readily understood by those persons skilled in the art that the present invention is susceptible of broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A device for shielding an area of a user's body, comprising:
    a protective member having a substantially rigid frame, a plurality of manually bendable rigid support legs extending from said protective frame in bendably adjustable angular relation thereto toward the body of the user, each of said legs terminating in a contact end, and a plurality of contact elements disposed on the contact ends of said support legs for contacting the body of the user; and
    a flexible support loop element attached to said protective member and forming a loop for placing around the neck of the user, whereby said protective member is suspended from the user's neck and positioned over said area to be shielded.

2. The device of claim 1, wherein each of said contact elements includes a contact face comprising a surface having a convex curvature for contacting the body of the user.

3. The device of claim 2, wherein said surface of said contact face has a relatively low coefficient of friction for contacting the body of the user in substantially non-frictional engagement.

4. The device of claim 1, further comprising a substantially rigid lightweight panel attached to said frame.

5. The device of claim 4, wherein said lightweight panel is perforated.

6. The device of claim 2, wherein each of said contact elements includes a disc-shaped member on which said respective contact face is formed.

7. The device of claim 1, wherein said support loop element includes two ends, each of said support loop element ends is attached to one of said support legs at a connection point located substantially adjacent said contact element on said leg, whereby said connection point forms a fulcrum point to assist in holding said protective member against the body of the user by gravity.

8. The device of claim 1, wherein said frame is bendably deformable for adjustment thereof by the wearer.

9. A device for shielding an area of a user's body, comprising:
    a protective member having a substantially rigid frame forming the perimeter of a quadrilateral with rounded corner portions, a pair of cross-piece members, each of said cross-piece members being attached to said frame at opposing corner portions and bisecting said perimeter of the quadrilateral shape, four substantially rigid support legs, each of said support legs formed integrally with one of said cross-piece members and extending from said one cross-piece member at one of said corner portions toward the body of the user and terminating in a contact end, and four contact elements for contacting the body of the user, each of said elements disposed on the contact end of one of said support legs; and
    a flexible support loop element forming a loop for placing around the neck of the user and having two ends, each of said ends being attached to a separate one of said support legs, whereby said protective member is suspended from the user's neck and positioned over said area to be shielded.

10. A device for shielding an area of a user's body, comprising:
    a protective member having:
        a substantially rigid frame, said frame comprising a lightweight rod material forming the perimeter of a quadrilateral having rounded corner portions;
        four substantially rigid support legs, each of said support legs extending from said protective frame in angular relation thereto toward the body of the user and terminating in a contact end;
        four contact elements for contacting the body of the user, each of said elements disposed on the contact end of one of said support legs and including a disc-shaped member having a contact face comprising a surface with a convex curvature and a relatively low coefficient of friction for contacting the body of the user in substantially non-frictional engagement; and
    a flexible support loop element forming a loop for placing around the neck of the user and having two ends, each of said ends being attached to a separate one of said support legs, whereby said protective member is suspended from the user's neck and positioned over said area to be shielded.

* * * * *